United States Patent [19]

Rizvi et al.

[11] Patent Number: 5,248,445
[45] Date of Patent: Sep. 28, 1993

[54] STABLE CONDITIONING SHAMPOO CONTAINING FATTY ACID

[75] Inventors: Riaz Rizvi, Glendale Heights; Chaitanya Patel, Glen Ellyn, both of Ill.

[73] Assignee: Helene Curtis, Inc., Chicago, Ill.

[21] Appl. No.: 905,738

[22] Filed: Jun. 29, 1992

Related U.S. Application Data

[63] Continuation-in-part of Ser. No. 828,028, Jan. 30, 1992.

[51] Int. Cl.$^5$ ............................................. C11D 17/00
[52] U.S. Cl. ................... 252/174.15; 252/170; 252/547; 252/550; 252/551; 252/554; 252/559; 252/DIG. 13; 424/70
[58] Field of Search ............... 252/174.15, 170, 547, 252/550, 551, 554, 559, DIG. 13; 424/70

[56] References Cited

U.S. PATENT DOCUMENTS

| | | | |
|---|---|---|---|
| 4,701,322 | 10/1987 | Dixon et al. | 424/70 |
| 4,997,641 | 3/1991 | Hartnett et al. | 252/550 |
| 5,034,218 | 7/1991 | Duvel | 252/547 |
| 5,106,613 | 4/1992 | Hartnett et al. | 252/174.21 |
| 5,114,706 | 5/1992 | Duvel | 252/174.23 |

FOREIGN PATENT DOCUMENTS

0407042A2 1/1991 European Pat. Off.

*Primary Examiner*—Patrick P. Garvin
*Assistant Examiner*—E. D. Irzinski
*Attorney, Agent, or Firm*—Marshall, O'Toole, Gerstein, Murray & Borun

[57] ABSTRACT

A conditioning shampoo containing an anionic surfactant, a long-chain fatty acid, and a non-volatile silicone material has extended product stability, excellent cleansing and foaming properties, and provides excellent and improved overall conditioning to human hair, particularly superior wet and dry combing properties.

20 Claims, No Drawings

5,248,445

STABLE CONDITIONING SHAMPOO CONTAINING FATTY ACID

CROSS REFERENCE TO RELATED APPLICATION

This application is a continuation-in-part of copending application Ser. No. 07/828,028, filed Jan. 30, 1992 and still pending.

FIELD OF INVENTION

The present invention is directed to a hair conditioning shampoo composition and to a method of treating hair with the composition to cleanse the hair and, at the same time, to provide the hair with improved wet-stage and dry-stage conditioning properties as well as other conditioning properties, such as softness, without residual buildup of conditioning agents on the hair. More particularly, the present invention is directed to a hair conditioning shampoo composition including one or more anionic cleaning surfactants, such as ammonium lauryl sulfate; one or more non-volatile silicone oils, such as a polydimethylsiloxane compound; a long-chain fatty acid; and, optionally, a water-insoluble, oil-soluble di-long-chain alkyl, quaternary ammonium salt conditioning agent.

BACKGROUND OF THE INVENTION AND PRIOR ART

Soiled human hair is shampooed to remove sebum that is naturally secreted by the head, as well as soil and other atmospheric contaminants that accumulate on the hair. Sebum, in particular, accumulates on the hair in a relatively short period of time leaving the hair with a greasy, dirty feel and poor manageability. The most effective shampoos for cleansing the hair for removal of the atmospheric contaminants and sebum are those that contain high lather synthetic anionic detergents, such as the long-chain alkyl sulfates and the partially ethoxylated long-chain alkyl sulfates. These synthetic anionic detergents are very effective for cleansing the hair but, after rinsing with water, leave the hair with a dried touch, usually called "creak" and result in hair, when wet, that is in an extremely tangled and unmanageable after-shampoo condition.

Thoroughly cleansed hair is extremely difficult to comb in either the wet or dry state because the individual hair fibers tend to snarl, kink, and interlock with each other. Particularly prior to complete drying of thoroughly cleansed hair in this after-shampoo stage the hair is very difficult to comb or brush. Even after complete drying, the thoroughly cleansed hair remains difficult to comb or brush and does not set well. Thoroughly clean, dried hair also has undesirable electrostatic properties in a low humidity atmosphere that causes the hair to "fly away," thereby further reducing the combing or brushing property of the hair. Generally, these above-outlined problems that result from synthetic detergent cleansing of the hair, particularly the high-lather synthetic anionic detergents, have been elevated either by the after-shampoo treatment of the hair with hair conditioners, for example in the form of a hair rinse, or by including hair conditioners directly within the shampoo composition.

After-shampoo hair conditioning compositions are easily formulated but are inconvenient to use because of the necessity of applying the conditioner to the hair in a separate stage after shampooing. The preparation of a conditioning shampoo has been more difficult because of inherent incompatibility problems between anionic surfactants and the fatty cationic compounds that are good conditioning agents. Contact between an anionic surfactant and a cationic surfactant or cationic polymer produces a precipitate that forms immediately or causes an interaction between the anionic and cationic compounds that significantly reduces their respective cleaning and conditioning properties. The reduction in cleansing and conditioning effectiveness is observed even in compositions wherein the anionic and cationic compounds do not precipitate from the composition but remain in solution or suspension. This incompatibility between an anionic surfactant and a cationic conditioning compound is well recognized by those skilled in the art. For example, Safarin in *Cosmetics*, Interscience Publishers, Inc., New York, p. 538 (1957), states that anionic and cationic compounds cannot be used in combination because they react to form insoluble salts.

A partial solution to this incompatibility problem in the formulation of conditioning shampoos is exemplified by the following patents that disclose compositions that contain surfactants that are not anionic, e.g., nonionics, amphoterics and zwitterionics, together with cationic conditioning compounds: U.S. Pat. No. 3,849,348 to Hewitt; U.S. Pat. No. 3,990,991 to Gerstein; and U.S. Pat. No. 3,822,312 to Sato. Published European Patent Application EP 0 407 042 A2 teaches long-chain alcohols, long-chain ethoxylated alcohols and/or long-chain esters or acids in conditioning shampoos.

Another problem inherent in formulating a conditioning shampoo is an instability problem that results when water-insoluble conditioning agents are also included in the conditioning shampoo composition, such as the non-volatile silicones that are well recognized in the art as providing a degree of softness to the hair.

Silicones in shampoo compositions have been disclosed in a number of different patents: U.S. Pat. No. 2,826,551, Mar. 11, 1958 to Green; U.S. Pat. No. 3,964,500, Jun. 22, 1976 to Drakoff; U.S. Pat. No. 4,364,837, Dec. 21, 1982 to Pader; British Patent No. 849,433, Sep. 28, 1960 to Woolston; U.S. Pat. No. 4,741,855 to Grote et al.; U.S. Pat. Nos. 4,788,006 and 4,902,449 to Bolich, Jr. et al.; and U.S. Pat. No. 4,704,272 to Oh et al.

A particularly difficult problem to solve in silicone-containing conditioning shampoos is that of keeping a dispersed, water-insoluble, non-volatile silicone material suspended in stable form while retaining the cleansing, particularly foam volume, and conditioning performance of the conditioning shampoo. A variety of materials have been proposed for inclusion in silicone-containing conditioning shampoos for purposes of thickening and stabilization such as xanthan gum, long-chain acyl derivatives, long-chain amide oxides, and long-chain alkanolamides as disclosed in U.S. Pat. Nos. 4,788,006, 4,704,272, and 4,741,855. The compositions of the present invention are stable and have increased foam volume and conditioning properties without amine oxide or acyl derivative suspending agents.

SUMMARY OF THE INVENTION

In accordance with the principles of the present invention, it has been found, surprisingly, that a conditioning shampoo containing an anionic surfactant, a long-chain fatty acid, particularly a long-chain ($C_{18}$–$C_{36}$) fatty acid that contains predominantly at least about 5%, preferably about 20% to about 90% by weight, behenic ($C_{22}$) acid; and a non-volatile silicone material has extended product stability, excellent cleansing and foaming properties, and provides excellent and improved overall conditioning to human hair, particularly superior wet and dry combing properties.

Hair treated with the composition of the present invention is thoroughly cleansed with increased foam and exhibits improved physical and cosmetic properties, such as gloss, thickness, manageability, and softness and body. Further, it was surprisingly and unexpectedly found that hair treated with the composition of the present invention does not experience buildup on the hair shaft, over time, of conditioning agents, as is common with many conditioning shampoo compositions.

Therefore, an aspect of the present invention is to provide a hair-treating composition that cleanses the hair, provides improved foam volume, and imparts improved physical properties and cosmetic properties to the hair in a single application.

Another aspect of the present invention is to provide a physically stable conditioning shampoo containing an anionic surfactant and a non-volatile silicone.

Another aspect of the present invention is to provide a new and improved conditioning shampoo containing a strong anionic detergent. such as a long-chain alkyl sulfate, long-chain alkyl ether sulfate, and/or long-chain sulfonate; a non-volatile silicone conditioning agent; and a long-chain ($C_{18}$–$C_{36}$) fatty acid to provide improved foaming. wet and dry conditioning. and stability.

Still another aspect of the present invention is to provide a new and improved conditioning shampoo including about 5% to about 65% of an anionic surfactant: optionally, about 0.1% to about 20% of a cationic, nitrogen containing conditioning agent having only two long-chain alkyl radicals bonded to the nitrogen atom, the long-chain radicals having predominantly about 12 to about 22 carbon atoms per long-chain alkyl radical. about 0.5% to about 10% of a non-volatile silicone material, and about 0.5% to about 10% of a long-chain fatty acid having at least 5% by weight behenic acid.

A further aspect of the present invention is to provide a new and improved method of making an aqueous conditioning shampoo having an anionic surfactant, optionally a cationic nitrogen-containing conditioning agent, a suspended non-volatile silicone, and a fatty acid by vigorously mixing the composition, together with the fatty acid, to suspend silicone droplets having a particle size in the range of about 5 microns to about 100 microns to provide new and unexpected stability to the conditioning shampoo composition without sacrifice in foaming.

The above and other aspects and advantages of the present invention will become apparent from the following detailed description of the preferred embodiments.

DETAILED DESCRIPTION OF THE PREFERRED EMBODIMENTS

The aqueous conditioning shampoo composition of the present invention generally includes an anionic surfactant in an amount of about 5% to about 65% by weight of the composition; a long-chain ($C_{18}$–$C_{36}$) fatty acid in an amount of about 0.5% to about 10% by weight of the composition; one or more non-volatile silicone conditioning agents in an amount of about 0.5% to about 10% by weight of the composition; and optionally, a cationic di-long-chain alkyl quaternary ammonium salt in the amount of about 0.1% to about 20% by weight of the composition.

The conditioning shampoo of the present invention provides the hair with improved foam, as well as improved physical and cosmetic conditioning properties, such as gloss, thickness, softness, and manageability, including excellent wet and dry combing properties and body. The composition of the present invention remains stable, while achieving excellent cleansing, foaming, and conditioning.

The anionic cleansing surfactant used in the composition and method of the present invention can be any of the anionic surfactants known or previously used in the art of hair shampoos. An anionic cleansing surfactant should be included in the composition of the present invention to effectively cleanse the hair and generates a high, stable foam level that consumers equate with cleaning efficiency. Nonionic and amphoteric surfactants are not as effective in cleansing the hair and do not provide the high foam level desired by consumers. However, optionally, nonionic, amphoteric, and/or zwitterionic surfactants can be included in the compositions of the present invention in addition to one or more anionic surfactants to help stabilize foam, to provide a suitable viscosity, or to give other functional or esthetic properties to the composition.

Usually, the anionic cleansing surfactant includes a hydrophobic moiety, such as a carbon chain including from about 8 carbon atoms to about 30 carbon atoms, and particularly from about 12 carbon atoms to about 20 carbon atoms, and further includes a hydrophilic moiety, such as a sulfate, sulfonate, carbonate, phosphate, or carboxylate. Often, the hydrophobic carbon chain is etherified, such as with ethylene oxide or propylene oxide, to impart a particular physical property, such as increased water-solubility or reduced surface tension, to the anionic cleansing surfactant.

Suitable anionic cleansing surfactants include. but are not limited to, compounds in the classes known as alkyl sulfates, alkyl ether sulfates, alkyl ether sulfonates, sulfate esters of an alkylphenoxy polyoxyethylene ethanol, alpha-olefin sulfonates, beta alkyloxy alkene sulfonates, alkyl arylsulfonates, alkyl carbonates, alkyl ether carboxylates, fatty acids, succinamates, sulfosuccinates, sarcosinates, octoxynol or nonoxynol phosphates, taurates, fatty taurides, sulfated monoglycerides, fatty acid amino polyoxyethylene sulfates, and isothienates, or combinations thereof. Many additional anionic cleansing surfactants are described in McCUTCHEON'S DETERGENTS AND EMULSIFIERS, 1989 ANNUAL, published by McCutcheon's Division MC Publishing Company, herein incorporated by reference. Usually, the anionic cleansing surfactant is present in the composition as a neutralized salt in the form of a sodium, potassium, lithium, ammonium, alkylammonium, or hydroxyalkylammonium salt, wherein the alkyl moiety includes from 1 to about 3 carbon atoms. The alkyl sulfates and alkyl ether sulfates are particularly effective classes of anionic cleansing surfactants. Exemplary anionic cleansing surfactants that are useful in the composition and method of the present invention include. but are not limited to, the ammonium, monoethanolamine, diethanolamine, triethanolamine, isopropylamine, sodium, potassium, lithium, or magnesium salts of lauryl sulfate, dodecylbenzenesulfonate, lauryl sulfosuccinate, lauryl ether sulfate, lauryl ether carboxylate, lauryl sarcosinate, cocomethyl tauride, and sulfosuccinate half ester amide, or combinations thereof. An especially useful anionic cleansing surfactant is a mixture of a lauryl sulfate salt and a lauryl ester sulfate salt.

To achieve the full advantage of the present invention, new and unexpected foaming, conditioning, and/or stabilization are achieved in the conditioning shampoos of the present invention by including at least about 5.0% by weight, preferably about 20% to about 90% by weight, behenic ($C_{22}$) acid in the long-chain fatty acid ($C_{18}$–$C_{36}$) such that the behenic acid is included in an amount of at least 0.10% by weight of the composition. The behenic acid is included in an amount of about 5% to about 100%, based on the total weight of the fatty acids ($C_{18}$–$C_{36}$ fatty acids) in the composition, preferably about 20% to about 90% based on the total weight of behenic acid and other $C_{18}$–$C_{36}$ fatty acids.

It is well known that the inclusion of a substantial amount, e.g., 1.5% or more, of silicone conditioning agents in a conditioning shampoo substantially lowers the amount of foam generated by strong anionic detergents (e.g., alkyl sulfates, alkyl sulfonates, alkyl ether sulfates, and alkyl ether sulfonates). Accordingly, anionic detergents have been included in a higher percentage in shampoos containing silicone conditioning agents, and/or foam boosters have been added to the conditioning shampoos to provide the consumer with high foaming levels that most consumers perceive as essential to good cleansing. In addition to the decrease in foaming resulting from the inclusion of silicone and other conditioning agents present in a conditioning shampoo, suspending agents used to suspend the conditioning agent(s) also have detracted from the foaming levels achieved and sometimes have lowered the conditioning benefits imparted by the conditioning agent(s). Some of the suspending agents that lower foam levels and conditioning benefits include the acyl derivatives, amine oxides and the like, as disclosed in the Grote U.S. Pat. No. 4,741,855, hereby incorporated by reference.

The conditioning shampoos of the present invention achieve excellent conditioning, foaming, and stability without the acyl derivatives or amine oxides disclosed to be necessary for stability in Grote U.S. Pat. No. 4,741,855. The ability to provide a conditioning shampoo that has excellent conditioning benefits, as well as excellent foaming and stability, has been a long-felt need in the conditioning shampoo art. The conditioning shampoos of the present invention solve this long-felt need by including a long-chain ($C_{18}$–$C_{36}$) fatty acid, containing at least about 5% behenic acid, preferably about 20% to about 90% by weight behenic acid, to stabilize the suspension.

In accordance with another important feature of the preferred embodiment of the present invention, the behenic acid, in an amount of at least about 0.5% by weight of the conditioning shampoo composition, provides pearlescence to the conditioning shampoo thereby increasing the stability of the composition as well as enhancing appearance. The behenic ($C_{22}$) acid can be added as straight acid, together with Montan Wax Acid ($C_{18}$–$C_{36}$) fatty acids or from a mixture of long-chain fatty acids, e.g., SYNCROWAX AW1-C ($C_{18}$–$C_{36}$) fatty wax acids containing about 75% $C_{22}$ saturated wax acid and about 25% $C_{18}$, $C_{20}$, and $C_{24}$–$C_{36}$ acids. The behenic $C_{22}$ acid is the important portion of the SYNCROWAX and can be used as the carboxylic acid.

In accordance with a preferred embodiment of the present invention, it has been found that a weight ratio of strong anionic alkyl ether detergents to all strong anionic detergents present in the composition of at least about 0.12, e.g., the ratio of ammonium laureth ether sulfate and/or ammonium laureth ether sulfonate, having 2 moles of ethoxylation, to ammonium lauryl sulfate and/or ammonium lauryl sulfonate, provides exceptional stabilization of the suspended, water-insoluble conditioning agents while maintaining excellent foam and conditioning benefits. In the preferred embodiment, the ethoxylated sulfate and/or ethoxylated sulfonate should be at least 12% and up to about 90% by weight of the total of ethoxylated and non-ethoxylated strong anionic detergents. To achieve the full advantage of the present invention, the alkyl ether sulfate and/or alkyl ether sulfonate should be present in an amount of about 2% to about 15% by weight of the composition and the alkyl sulfate and/or alkyl sulfonate in an amount of about 5% to about 20% by weight of the composition.

Foam boosters can be added to the compositions of the present invention to further increase the foam volume attributed by the anionic and other detergents. Suitable foam boosters include, for example, polyvinylpyrrolidone (PVP); polyox; cetyl betaine; cocamide; cocamidoethyl betaine; cocamidopropyl betaine; cocamidopropyl hydroxysultaine; cocoamphodipropionic acid; coco-betaine; coco/oleamidopropyl betaine; coco-sultaine; cocoyl hydroxyethyl imidazoline; DEA-cocoamphodipropionate; DEA-lauraminopropionate; decyl betaine; disodium isostearyl sulfosuccinate; isopropyl stearate; lauramide; lauramidopropyl betaine; lauryl betaine; lauryl sultaine; myristamidopropyl betaine; myristaminopropionic acid; myristyl betaine; oleamidopropyl betaine; oleamidopropyl hydroxysultaine; oleyl betaine; palmamidopropyl betaine; palmitamidopropyl betaine; PEG-6 cocamide; PEG-3 lauramide; PEG-5 lauramide; PEG-6 lauramide; sodium cocoamphoacetate; sodium cocoamphopropionate; sodium lauraminopropionate; sodium lauroamphopropionate; sodium lauroyl sarcosinate; sodium myristoamphoacetate; sodium myristoyl sarcosinate; TEA-hydrogenated tallow glutamate; TEA-lauraminopropionate; TEA-myristaminopropionate; and undecylenamidopropylamine oxide.

To achieve the full advantage of the present invention, a nonionic alkanolamide optionally is included in the conditioning shampoo composition in an amount of about 0.1% to about 5% by weight to provide exceptionally stable emulsification of water-insoluble conditioning agents and to aid in thickening and foam stability. Other useful suspending and thickening agents can be used instead of the alkanolamides such as sodium alginate, guar gum, xanthan gum, gum arabic, cellulose derivatives, such as methylcellulose, hydroxybutylcellulose, hydroxyethylcellulose, hydroxypropylcellulose, and carboxymethylcellulose, and various synthetic polymeric thickeners, such as the polyacrylic acid derivatives. Suitable alkanolamides include, but are not limited to, those known in the art of hair care formulations, such as cocamide monoethanolamide (MEA), cocamide diethanolamide (DEA), soyamide DEA, lauramide DEA, oleamide monoisopropylamide (MIPA), stearamide MEA, myristamide MEA, lauramide MEA, capramide DEA, ricinoleamide DEA, myristamide DEA, stearamide DEA, oleylamide DEA, tallowamide DEA, lauramide MIPA, tallowamide MEA, isosteramide DEA, isostearamide MEA, and combinations thereof.

The composition of the present invention also includes from about 0.15% to about 10%, and preferably from about 1.0% to about 5.0%, by weight of a nonvolatile silicone compound. The preferred non-volatile silicone compound is a polydimethylsiloxane compound, such as a mixture, in about a 3:1 ratio, of a low molecular weight polydimethysiloxane fluid and a higher molecular weight polydimethylsiloxane gum. The non-volatile polydimethylsiloxane compound is added to the composition of the present invention in an amount sufficient to provide improved combing and improved feel (softness) to the hair after shampooing. As referred to herein, "silicone gums" are those non-functional siloxanes having a viscosity of from about 5 to about 600,000 centistokes at 25° C. The so-called rigid silicones, as described in U.S. Pat. No. 4,902,499, herein incorporated by reference, having a viscosity above 600,000 centistokes at 20° C., e.g., 700,000 centistokes plus and a weight average molecular weight of at least about 500,000 also are useful in accordance with the present invention.

Preferred silicone gums include linear and branched polydimethyl siloxanes of the following general formula:

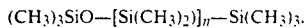

wherein n is from about 2,000 to about 15,000, preferably from about 2,000 to about 7,000. Silicone gums useful in compositions of the present invention are available from a variety of commercial sources, including General Electric Company and Dow Corning.

In one embodiment, the emulsified conditioning shampoo of the present invention also includes a cationic water-insoluble, emulsifiable conditioning agent. The cationic conditioning agent used in the emulsified conditioning composition and method of the present invention is an oil-soluble, water-dispersible di-long-chain alkyl, di-short-chain alkyl quaternary ammonium salt. Oil-soluble, water-dispersible quaternary ammonium compounds useful in the composition and method of the present invention are quaternary ammonium compounds having two long-chain alkyl groups including from about 12 to about 22 carbon atoms. The long chains can be predominantly 12, 14, 16, 18, 20, and/or 22 carbon atoms in length and can be only one chain length or can be mixed chain lengths. The remaining two substitutions present on the quaternary nitrogen of the quaternary ammonium compound can be hydrogen, benzyl, short-chain alkyl groups, having 1 to 4 carbon atoms such as methyl, ethyl, or hydroxyethyl, or combinations thereof, as long as the quaternary ammonium compound is oil soluble and water dispersible and contains two long-chain alkyl substitutions as defined.

The anion of the oil-soluble quaternary ammonium compound can be any anion, such as chloride, bromide, methyl sulfate, acetate, phosphate, or nitrate, as long as the quaternary ammonium compound is oil soluble.

In accordance with one embodiment of the present invention, the composition includes an oil-soluble, water-dispersible conditioning agent having a quaternary nitrogen atom and two long alkyl chains, having from about 12 to about 22 carbon atoms per alkyl chain. These conditioning agents include a wide range of compounds that can be broadly divided into groups based upon the structure of the substitution on the quaternary nitrogen atom, i.e., (a) compounds having two long carbon chains and one or two identical or different short-chain alkyl groups having one to four, particularly one or two, carbon atoms, and (b) compounds having two long carbon chains, one benzyl group, and one short-chain alkyl group having one to four, particularly one or two, carbon atoms. The following list of oil-soluble quaternary ammonium compounds are exemplary, but not limiting, of oil-soluble, di-long-chain alkyl quaternary ammonium compounds that can be used in the composition and method of the present invention.

| | |
|---|---|
| Distearyldimethyl-ammonium chloride | (Distearyl dimonium chloride); |
| Distearyldimethyl-ammonium bromide | (Distearyl dimonium bromide) |
| Dicetyldimethyl-ammonium bromide | (Dicetyl dimonium bromide); |
| Dimethyldi-(hydrogenated tallow)-ammonium chloride | (Quaternium-18); |
| Dicetylmethylbenzyl-ammonium chloride; | |
| Dicetyldimethyl-ammonium chloride | (Dicetyl dimonium chloride); |
| Dicocodimethyl-ammonium chloride | (Dicoco dimonium chloride); |
| Dicocodimethyl-ammonium bromide | (Dicoco dimonium bromide); |
| Dibehenyl/diarachidyl-dimethyl ammonium chloride | (Dibehenyl/diarachidyl dimonium chloride); |
| Dibehenyl/diarachidyl-dimethyl ammonium bromide | (Dibehenyl/diarachidyl dimonium bromide); |
| Dibehenyl dimonium methyl sulfate | (Dibehenyl dimonium methyl sulfate); |
| Hydroxypropyl bis-stearyl-ammonium chloride | (Hydroxypropyl bis-stearyl dimonium chloride); |
| Dibehenyldimethyl-ammonium chloride. | (Dibehenyl dimonium chloride); |
| Dibehenylmethyl-benzyl-ammonium chloride; | |
| Dimyristyldimethyl-ammonium bromide; | (Dimyristyl dimonium bromide); |
| Dimyristyldimethyl-ammonium chloride | (Dimyristyl dimonium chloride); | wherein the name in parenthesis is the compound name given in the CTFA Dictionary.

It should be noted that the long alkyl chains of the oil-soluble quaternary ammonium compound are not commonly of a single chain length, but a mixture of chain lengths primarily with the $C_{12}$–$C_{22}$ range, e.g., $C_{12}$, $C_{14}$, $C_{16}$, $C_{18}$, $C_{20}$, and/or $C_{22}$. Generally, the oil-soluble quaternary ammonium compounds used in the compositions of the present invention have the long alkyl chains as a mixture of alkyl lengths. Such di-long-chain alkyl quaternary ammonium compounds function in accordance with the principles of the present invention as long as the quaternary ammonium compound is oil-soluble and water-dispersible. Such conditioning agents are prepared conveniently from naturally-occurring materials, such as tallow, coconut oil, soya oil, and the like, or from synthetically-produced mixtures which are known to include a mixture of long-chain radicals.

The water-insoluble emulsifiable conditioning agent useful in the present invention should have the ability to separate from water and form a two-phase composition in water when the conditioning agent is mixed with water, prior to emulsification of the composition of the present invention. To achieve the full advantage of the present invention, the water-insoluble, emulsifiable quaternary ammonium conditioning agents used in the compositions of the present invention have a water-solubility of less than 1%. Such agents may be employed either as liquids or as solids.

To achieve the best stability, the water and the anionic surfactant(s) are mixed first and heated to a temperature above the melting point of the fatty acid, e.g., 150°–200° F. The fatty acid then is added until completely dissolved in the water. The silicone or silicone blend then can be added and the mixture is agitated vigorously to shear and break up the silicone material into droplets preferably to a size less than about 10 micrometers, and more preferably to a size of about 5 microns to about 100 microns. The mixture is maintained at a temperature above the melting point of the fatty acid until all components are added.

To achieve the best results at the point that the silicone is sheared, the composition should have a viscosity in the range of about 2,000 to about 20,000 centipoises so that upon vigorous mixing or shearing, the resulting silicone droplets have a particle size of about 5 microns to about 100 microns, and preferably about 10 microns to about 30 microns, and are stable in the oil phase. As an example of the vigorous mixing, a six-bladed axial flow turbine impeller rotating at a speed of about 500 to 800 r.p.m. provides sufficient shearing of the non-volatile silicone material resulting in silicone droplets within the size range of about 5 to about 100 microns, and the sheared silicone droplets are exceptionally stable. The shearing of the silicone within a viscous composition provides the best silicone particle size and stability to the composition. If the particle size of the silicone droplets is less than about 5 microns, the total silicone surface area is too great resulting in reduced foam. If the particle size of the silicone droplets is greater than about 100 microns, the silicone droplets have a tendency to coalesce and separate from the composition.

Other common cosmetic components and additives can be included in the compositions of the present invention, as long as the basic properties of the hair shampoos and shampoo conditioners are not adversely affected. Such optional cosmetic components and additives include, but are not limited to; nonionic surfactants, amphoteric surfactants, fragrances, dyes, hair colorants, opacifiers, pearlescing agents, thickeners, dandruff-control agents, hydrotropes, foam stabilizers, solubilizers, preservatives, water-softening agents, acids, alkalis, buffers, and the like. These optional components and additives usually are present in weight percentages of less than about 5% by weight each, and usually from about 0.1% to about 20% by weight of the composition in total.

For example, to improve consumer acceptance, both skin mildness and enhanced composition esthetics can be achieved by optionally including polyvinyl pyrrolidone and/or an amphoteric surfactant in the hair shampoo/conditioner in an amount ranging from 0% to about 5% by weight of the composition.

Suitable amphoteric surfactants that can be included in the compositions of the present invention include, but are not limited to, betaines, and hydroxypropylsultaines, or combinations thereof. Examples of amphoteric surfactants include, but are not limited to, cocamidopropyl betaine, lauramidopropyl betaine, coco/oleamidopropyl betaine, coco betaine, oleyl betaine, cocamidopropyl hydroxysultaine, tallowamidopropyl hydroxysultaine and dihydroxyethyl tallow glycinate, or combinations thereof. In general, any amphoteric surfactant can be included in the composition of the present invention as long as the stability, the conditioning, and the cleansing efficiency of the composition are not adversely affected.

The hair shampoo/conditioner compositions of the present invention also can include nonionic surfactants to help impart esthetic, physical, or cleansing properties to the composition. Likewise, the compositions can include other emulsifiers, conditioning agents, inorganic salts, humectants, and similar materials to provide the composition with desirable esthetic or physical properties. Generally, such optional ingredients are present in weight percentages of from about 0% to about 5% each, and from about 0% to about 20% in total, relative to the total weight of the composition.

The carrier of the hair shampoo/conditioner composition of the present invention is predominantly water, but non-aqueous solvents also can be included to help solubilize composition ingredients that are not sufficiently soluble in water, to adjust the viscosity the composition or to act as a humectant. Suitable solvents include polyols, like glycerol, glycols, like ethylene glycol, propylene glycol and hexylene glycol, or mixtures thereof. The optional non-aqueous solvents should not adversely affect the ability of the composition to cleanse and condition the hair or adversely affect consumer appeal of the composition. A non-aqueous solvent can be present in the hair shampoo/conditioner composition of the present invention in an amount ranging from about 0% to about 5% by weight of the composition.

To achieve the full advantage of the present invention, the hair shampoo/conditioner composition is a relatively viscous mixture, e.g., about 3000 to about 8000 centipoises at 25° C., that is stable indefinitely at temperatures normally found in commercial product storage and shipping. A composition of the present invention, either opacified or pearlescent, is stable to phase separation and precipitation of composition ingredients at a temperature of about 20° C. to about 25° C. essentially indefinitely. The compositions also have demonstrated sufficient stability to phase separation or precipitation of ingredients at temperatures normally found in commercial product storage and shipping to remain unaffected for periods of one year or more.

The following examples illustrate conditioning shampoos made in accordance with the present invention:

| | EXAMPLE 1 | |
|---|---|---|
| Item # | Description | Actual Wt. % |
| 1 | DEIONIZED WATER | 28.86978 |
| 2 | POLYVINYLPYRROLIDONE | 0.50000 |
| 3 | AMMONIUM LAURETH SULFATE (2 MOLES OF ETHOXYLATION) (30% ACTIVE) | 10.00000 |
| 4 | AMMONIUM LAURYL SULFATE, (30% ACTIVE) | 50.00000 |
| 5 | DISTEARYLDIMONIUM CHLORIDE | 0.30000 |
| 6 | COCAMIDE MEA | 1.50000 |
| 7 | BEHENIC ACID | 1.25000 |
| 8 | MONTAN ACID WAX (CONTAINS 5% BEHENIC ACID) | 1.25000 |
| 9 | LAURYL BETAINE, (40% ACTIVE) | 2.00000 |
| 10 | SILICONE BLEND (33% GUM/67% OIL) | 2.50000 |
| 11 | FRAGRANCE | 0.50000 |
| 12 | METHYLCHLOROISOTHIAZOLINONE/METHYLISOTHIAZOLINONE (PRESERVATIVE) | 0.08000 |

-continued

EXAMPLE 1

| Item # | Description | Actual Wt. % |
|---|---|---|
| 13 | TETRADOSIUM EDTA. (39% ACTIVE) (PRESERVATIVE) | 0.10000 |
| 14 | POLYSORBATE 20 (VISCOSITY MODIFIER) | 0.15000 |
| 15 | D&C RED #33 (COLOR) | 0.00002 |
| 16 | D&C ORANGE #4 (COLOR) | 0.00020 |

Add #1 into compounding tank.
Add #2. mix with high agitation.
Add #3 and #4; mix well. Begin heating to 180-185° F.
Add #5. mix until all of #5 is dispersed.
Add #6: mix well.
Add #7 and #8. mix until completely dissolved.
Continue heating batch to 180-185° F. Maintain temperature at 180-185° F. for one hour while mixing at high speed. Check to make certain that the batch is completely melted and uniform, then add #9, and begen cooling using moderate agitation.
Add #15 and #16 diluted 1:10 with deionized water.
Continue cooling the batch. At 110° F., increase agitation to high, without aerating, and add #10.
Mix until all of #10 is dispersed and uniform with batch.
Add #11, #12, #13 and #14. Mix well after each addition.
Stop cooling and mixing at 80° F.
Specifications:
VISCOSITY - 4000-6000 centipoises (Brookfield viscometer AP#5-0004.2D)
pH - 5.0-5.5

What is claimed is:

1. A hair conditioning shampoo composition comprising an emulsion of water; about 5 to about 65 percent by weight of an anionic cleaning surfactant; from about 0.1 to about 10% by weight of a silicone conditioning agent; from about 0.5 to about 20 weight percent of a long-chain fatty acid, having about 18 to 36 carbons in the long chain, wherein the long-chain fatty acid includes predominantly at least about 5% by weight behenic acid.

2. The hair conditioning shampoo composition according to claim 1, wherein said silicon conditioning agent includes a silicone oil and a silicone gum in an amount of about 1.5 to about 5% by weight of said composition.

3. The hair conditioning shampoo composition according to claim 1 further including a cationic di-long chain quaternary nitrogen-containing conditioning agent in an amount of about 0.1% to about 10% by weight of the composition.

4. The hair conditioning shampoo of claim 3, wherein the quaternary nitrogen-containing conditioning agent is a quaternary ammonium salt containing two alkyl radicals having a carbon chain length from about 12 to about 18 carbon atoms per radical.

5. The hair conditioning shampoo composition according to claim 3, wherein said quaternary nitrogen-containing conditioning agent is present at about 1% to about 3% by weight of the composition.

6. The hair conditioning shampoo composition according to claim 1, wherein said behenic acid is present in an amount of about 20% to about 90% by weight of fatty acids contained in said composition.

7. The composition of claim 1, wherein the silicone has a viscosity at 25° C. of at least 5 centistokes and a boiling point at 760 mm Hg pressure and 25° C. of at least 250° C.

8. The composition of claim 1, wherein the anionic cleaning surfactant is selected from the group consisting of alkyl sulfates; alkyl sulfonates; alkyl ether sulfates and alkyl ether sulfonates.

9. The hair conditioning composition according to claim 6, wherein said behenic acid is contained in the composition in an amount of at least about 0.1% by weight of the composition.

10. The hair conditioning composition according to claim 3, wherein said quaternary nitrogen-containing conditioning agent is selected from the group consisting of (a) compounds having two long carbon chains and two identical or different short chain alkyl groups containing one to four carbon atoms bonded to the quaternary nitrogen atom, (b) compounds having two long carbon chains, one benzyl group and one short chain alkyl group having one to four carbon atoms bonded to the quaternary nitrogen atom, and (c) compounds having two long carbon chains, one hydrogen atom and one short chain alkyl group having one to four carbon atoms bonded to the quaternary nitrogen atom.

11. In a hair conditioning shampoo composition containing water; a long-chain anionic detergent; a fatty acid; and a non-volatile silicone conditioning agent, the improvement comprising the fatty acid having about 18 to about 36 carbons in the long-chain and the fatty acid providing at least 0.1% by weight behenic acid to the composition.

12. In a hair conditioning shampoo as defined in claim 11, the improvement further comprising the long-chain anionic detergent including an alkyl sulfate and an alkyl ether sulfate and/or alkyl sulfonate and/or an alkyl ether sulfonate wherein the weight ratio of alkyl ether sulfate, plus alkyl ether sulfonate to alkyl sulfate, plus alkyl sulfonate, plus alkyl ether sulfate, plus alkyl ether sulfonate is at least 0.12.

13. A method of shampooing and conditioning hair which comprises applying to said hair a composition comprising an emulsion of water; about 5 to about 65 percent by weight of an anionic cleaning surfactant; from about 0.1 to about 10% by weight of a silicone conditioning agent; from about 0.5 to about 20 weight percent of a long-chain fatty acid, having about 18 to 36 carbons in the long chain, wherein the long-chain fatty acid includes predominantly at least about 5% by weight behenic acid.

14. A method of shampooing and conditioning hair which comprises applying to said hair a composition containing water; a long-chain anionic detergent; a fatty acid; and a non-volatile silicone conditioning agent, the improvement comprising the fatty acid having about 18 to about 36 carbons in the long-chain and the fatty acid providing at least 0.1% by weight behenic acid to the composition.

15. A method of manufacturing a conditioning shampoo composition comprising an emulsion of water; about 5 to about 65 percent by weight of an anionic cleaning surfactant; from about 0.1 to about 10% by weight of a silicone conditioning agent; from about 0.5 to about 20 weight percent of a long-chain fatty acid, having about 18 to about 36 carbons in the long chain, wherein the long-chain fatty acid includes predominantly at least about 5% by weight behenic acid comprising:

heating a mixture of water, and an anionic surfactant to a temperature above the melting point of the fatty acid;
adding the fatty acid to said heated water until said acid is completely melted to form an acid solution;
adding a silicone conditioning agent to the acid solution to form a two-phase composition; and vigorously agitating the two-phase composition to break up the silicone into droplets and suspend said silicone droplets.

16. The method of claim 15 further including adding a di-long chain alkyl quaternary nitrogen-containing conditioning agent before or after said vigorous agitation while maintaining the temperature of the two phase composition at or above the melting point of said conditioning agent to form a stable emulsion having a viscosity of about 2,000 centipoises to about 20,000 centipoises.

17. The method of claim 15, wherein said non-volatile silicone is present in an amount of about 1.5 to about 5% by weight of said composition.

18. The method of claim 16, wherein said quaternary nitrogen-containing conditioning agent is a quaternary ammonium salt containing two alkyl radicals having a carbon chain length from about 12 to about 18 carbon atoms per radical.

19. The method of claim 16, wherein said quaternary nitrogen-containing agent is present at to about 3% by weight of the composition.

20. The method of claim 15, wherein said behenic acid is present in an amount of about 0.1 to about 5 weight percent of said composition.

* * * * *

UNITED STATES PATENT AND TRADEMARK OFFICE
CERTIFICATE OF CORRECTION

PATENT NO.   :   5,248,445
DATED        :   SEPTEMBER 28, 1993
INVENTORS    :   RIZVI, ET AL.

It is certified that error appears in the above-identified patent and that said Letters Patent is hereby corrected as shown below:

Column 5, line 15, after "acids" delete "$(C_{18}[-C_{36}$" and substitute therefor -- $(C_{18}-C_{36}$ --;

Column 7, line 5, after "weight" delete "polydimethysiloxane" and substitute therefor -- polydimethylsiloxane --;

Column 9, lines 54-55, after "including" delete "polyvinyl pyrrolidone" and substitute therefor -- polyvinylpyrrolidone --;

Column 11, line 19, after "#9, and" delete "begen" and substitute therefor -- begin --;

Column 11, line 39, after "said" delete "silicon" and substitute therefor -- silicone --; and Column 14, line 9, after "at" insert -- about 0.1% --.

Signed and Sealed this

Ninth Day of August, 1994

Attest:

BRUCE LEHMAN

Attesting Officer

Commissioner of Patents and Trademarks